United States Patent
Poss et al.

(10) Patent No.: US 8,530,709 B2
(45) Date of Patent: Sep. 10, 2013

(54) PROCESS FOR THE PRODUCTION OF FLUORINATED ALKENES

(75) Inventors: Andrew Joseph Poss, Kenmore, NY (US); David Nalewajek, West Seneca, NY (US); Michael Van Der Puy, Amherst, NY (US); Haridasan K. Nair, Williamsville, NY (US)

(73) Assignee: Honeywell International Inc., Morristown, NJ (US)

( * ) Notice: Subject to any disclaimer, the term of this patent is extended or adjusted under 35 U.S.C. 154(b) by 300 days.

(21) Appl. No.: 13/110,992

(22) Filed: May 19, 2011

(65) Prior Publication Data

US 2011/0288349 A1 Nov. 24, 2011

Related U.S. Application Data

(60) Provisional application No. 61/347,164, filed on May 21, 2010.

(51) Int. Cl.
C07C 21/18 (2006.01)

(52) U.S. Cl.
USPC .......... 570/172; 570/134; 570/136; 570/156; 570/164; 570/165

(58) Field of Classification Search
None
See application file for complete search history.

(56) References Cited

U.S. PATENT DOCUMENTS

| | | | |
|---|---|---|---|
| 5,210,340 A | 5/1993 | Bielefeldt et al. | |
| 5,463,150 A | 10/1995 | Lui et al. | |
| 5,516,951 A | 5/1996 | Aoyama | |
| 5,608,128 A | 3/1997 | Nakada et al. | |
| 5,969,197 A | 10/1999 | Lui et al. | |
| 6,187,978 B1 | 2/2001 | Rygas et al. | |
| 8,143,462 B2 * | 3/2012 | Nappa | 570/156 |
| 2009/0156869 A1 | 6/2009 | Nappa | |

FOREIGN PATENT DOCUMENTS

| | | |
|---|---|---|
| JP | 58194826 A | 11/1983 |
| JP | 2010001244 A | 1/2010 |
| WO | 2009117458 A2 | 9/2009 |

OTHER PUBLICATIONS

Angelini, G., et al., Synthesis and tritium-induced fluorine-19 NMR shifts of 1,1,1,4,4,4-hexafluoro-2,3-ditritio-2-butene, Canadian Journal of Chemistry, 1992, pp. 1221-1228, vol. 70, No. 4, 1st. Chim. Nucl., CNR, Rome, Italy.
Leedham K. and Haszeldine, R. N., Addition of Free Radicals to Unsaturated Systems. Part VIII.* The Direction of Radical-addition to Alkyl- and Perfluoroalkyl-acetylenes., J. Chem. Soc., 1954, pp. 1634-1638.
Henne, Albert L, and Finnegan, William G., Perfluoro-2-butyne and its Hydrogenation Products, J. Am. Chem. Soc., 1949, vol. 71, pp. 298-300.
Haszeldine, R.N., The Addition of Free Radicals to Unsaturated Systems. Part I. The Direction of Radical Addition to 3:3:3-Trifluoropropene, J. Chem. Soc., 1952, pp. 2504-2513.
Rylander, P. N., Catalytic Hydrogenation over Platinum Metals, Chapter 4: Acetylenes, Academic Press, 1967.
Takei, S. and Ono, M., Nippon Nogei Kagaku Kaisi 18 (1942b) 119.
Hudlicky, M., Reductions in Organic Chemistry, 2nd Ed., ACS Monograph 188, 1996, p. 8.
Prakesch, M., Gree, D., and Gree, R., Synthesis of New Optically Active Propargylic Fluorines and Application to the Enantioselective Synthesis of Monolfuorinated Analogues of Fatty Acid Metabolites, J. Org. Chem., 2001, vol. 66, pp. 3146-3151.
Haszeldine, R.N., Rowland, R., Tipping, A.E., and Tyrrell, G., Reaction of Hexafluoropropene with Halogenoalkenes, J. Fluorine Chemistry, 1982, vol. 21, pp. 253-259.

* cited by examiner

*Primary Examiner* — Sudhakar Katakam
(74) *Attorney, Agent, or Firm* — Bruce O. Bradford; Erika S. Wilson

(57) ABSTRACT

The present invention provides a method for the preparation of suitable chlorofluorocarbon and hydrochlorofluorocarbon materials or chlorofluorocarbon and hydrochlorofluorocarbon alkene and alkyne intermediates which serve as useful feedstock for fluorination and reduction to cis-1,1,1,4,4,4-hexafluoro-2-butene. Also presented is a continuous process for the production of cis-1,1,1,4,4,4-hexafluoro-2-butene from the alkene and alkyne intermediates.

13 Claims, No Drawings

PROCESS FOR THE PRODUCTION OF FLUORINATED ALKENES

CROSS-REFERENCE TO RELATED APPLICATION

This application claims domestic priority from commonly owned, U.S. Provisional Patent Application Ser. No. 61/347,164, filed 21 May 2010, the disclosure of which is hereby incorporated herein by reference.

FIELD OF THE INVENTION

The present invention relates to a process for the preparation of fluorinated alkenes, and more specifically, the preparation of cis-1,1,1,4,4,4-hexafluoro-2-butene:

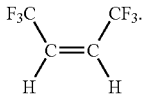

BACKGROUND OF THE INVENTION

Halofluorocarbon (where halo means Cl, Br, I or F) based fluids have found widespread use in industry in a number of applications, including as refrigerants, aerosol propellants, blowing agents, heat transfer media, and gaseous dielectrics. For example, halo-fluoroalkanes, such as chlorofluoromethane and chlorofluoroethane derivatives, have gained wide spread use as refrigerants owing to there unique combination of chemical and physical properties. Similarly, because of their properties, halofluoro-carbon materials such as fluoro-trichloromethane (CFC-11) had become standard materials for aerosols and foam blowing agents.

Because of suspected environmental problems associated with the use of some of these agents, including relatively high global warming potentials (GWP) associated therewith, it is desirable to use agents having the lowest possible GWP in addition to low, preferably zero, ozone depletion potential (ODP). Thus there is considerable interest in developing such environmentally friendlier materials.

One solution to this problem involved substituting a hydrogen containing chlorofluoroalkane (HCFC) in place of the CFC. For example, dichlorotrifluoroethane, $CHCl_2CF_3$ (HCFC-123), dichlorofluoromethane ($CHCl_2F$), and dichlorofluoroethane ($CH_3CCl_2F$) (HCFC-141b) were proposed as replacement agents. Over time, however, even these more environmentally acceptable materials were found to have shortcomings since they still contained chlorine and therefore still had an unacceptable ODP. Consequently, these materials have been targeted for eventual removal from use.

Recognizing the need to identify a non-chlorinated compound, hydrofluoro-carbon materials (HFCs) were identified as plausible replacements for the HCFCs. While the HFCs did not exhibit any substantial ODP values, they did have associated with them a global warming potential which presents a new set of issues for acceptance.

Because of the suspected environmental problems associated with the use of the various classes of compounds discussed above, it is desirable to continue to search for compounds having the lowest possible GWP and ODP. Thus there is considerable interest in developing environmentally friendlier materials for the applications mentioned above. One such class of compounds which meet the new needs are materials derived from a class of compounds referred to as fluoro-olefins and more specifically, fluorinated butenes.

However, while fluorinated butenes have zero ozone depletion values and very low global warming potential values, the toxicity, boiling point and other critical properties required to meet the applications specified above, can vary greatly from isomer to isomer. One particular isomer of fluorinated butenes which has the potential to fill many of the applications specified above is 1,1,1,4,4,4-hexafluoro-2-butene and more specifically, cis-1,1,1,4,4,4-hexafluoro-2-butene:

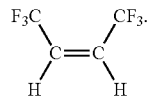

There are several methods for producing hexafluoro-2-butene, but such processes may give exclusively the trans-isomer. See, for example, the zinc reduction of 1,1,1,4,4,4-hexafluoro-2-iodobutene; K. Leedham and R. N. Hazeldine, J. Chem. Soc., 1954, 1634.

Processes that give a mixture of cis- and trans-isomers are likewise undesirable if a substantial proportion of the trans-isomer is formed. One reason is that the difference in boiling points for the two isomers is large (the trans-isomer boiling at about 9° C. and the cis-isomer boiling at about 32° C.). For applications that depend in large part on the boiling point of the fluorocarbon, the large difference in boiling points may mean that only one isomer is suitable and the other isomer therefore represents a yield loss. Another reason such a mixture is undesirable is that a good means for recycling the undesired trans-isomer is lacking. Ideally, a suitable process will provide the cis:trans isomers in a ratio of 10:1 or better.

Still other processes for cis-olefins suffer from co-production of the corresponding saturated alkane compound. In the present case, this means the co-production of 1,1,1,4,4,4-hexafluorobutane. This is likewise undesirable because it does not posses the low GWP that the corresponding butene does. Furthermore, like the trans-isomer, there is no convenient way to recycle this by-product.

One prior art method for making cis-1,1,1,4,4,4-hexafluorobutene (J. Am. Chem. Soc., 71, 1949, 298) involves reduction of hexafluoro-2-butyne with hydrogen (100 atmospheres) using Raney nickel catalyst at room temperature. Not only does this pressure require specialized equipment, but the conversion was only 82% and the product was a mixture of cis-hexafluoro-2-butene (41% yield) and hexafluorobutane (25% yield). Ideally the amount of over-reduced material should be less than 10%. Still more preferably, the total amount of trans-isomer and butane are together less than 10%.

R. N. Hazeldine, J. Chem. Soc., 1952, pp. 2504, also reported the reduction of hexafluorobutyne with Raney nickel at 60° C. and 15 atmospheres of hydrogen pressure to give cis-hexafluorobutene. Although some over-reduction to hexafluorobutane was mentioned, the yield of 91% is substantially better than the yield given in the reference cited above.

A few methods exist for the exclusive preparation of non-fluorinated cis-olefins to the exclusion of the corresponding trans-isomer. The most common of these is the catalytic reduction of alkynes. A number of catalysts may be employed for this transformation but they can, unfortunately, give a wide range of results and undesirable side reactions such as over-reduction to alkanes, formation of trans-olefins, and isomerization of cis to trans olefins. In addition, a wide range of variables can alter the results, such as temperature, mixing rate, solvent, and added reagents which may intentionally or unintentionally alter the reactivity of the catalyst.

For a general discussion of this chemistry see P. N. Rylander, Catalytic Hydrogenation over Platinum Metals, Chapter 4, Academic Press, 1967. For example, depending on the temperature, the reduction of acetylene dicarboxylic acid using Pd on $BaSO_4$ can give either succinic acid (no double bond) at −18° C. or maleic acid (cis double bond) at 100° C., while the ratios of cis to trans products for the reduction of p-methoxyphenylacetylene carboxylic acid with the same catalyst were similar (20%±5% trans isomer) over a wide temperature range. See, S. Takei and M. Ono, Nippon Nogei Kagaku Kaisi 18 (1942b) 119.

Catalysts that have been used for the selective reduction of non-fluorinated alkynes to alkenes include Pd/C, $Pd/BaSO_4$, $Pd/BaCO_3$, and $Pd/CaCO_3$. In order to achieve high selectivity, however, the use of quinoline as a catalyst modifier has been recommended whether the catalyst is Pd/C, $Pd/BaSO_4$, or Lindlar catalyst, $Pd/CaCO_3/Pb$. See, M. Hudlicky, Reductions in Organic Chemistry, $2^{nd}$ Ed., ACS Monograph 188, 1996, p 8.

The Lindlar catalyst is often used for the reduction of hydrocarbon alkynes to cis-alkenes, modified further by the addition of an aromatic amine such as quinoline or pyridine. The amines, while often useful in improving reaction selectivity, are not desirable from the standpoint of their toxicity. The quality of the quinoline used may also affect the outcome. The $Pd/CaCO_3/Pb$ catalyst, modified with pyridine, was successfully used in the reduction of an alkyne bearing a single fluorine on the carbon adjacent to the triple bond to give the corresponding cis-alkene. See, M. Prakesch, D. Gree, and R. Gree, J. Org. Chem., 66 (2001) 3146.

As is well known in the art, however, fluorocarbons often behave quite differently compared to non-fluorinated alkanes, and perfluorinated compounds may behave quite differently than even partially fluorinated compounds of similar structure.

SUMMARY OF THE INVENTION

The present invention provides a method for the preparation of suitable chlorofluorocarbon and hydrochlorofluorocarbon materials or chlorofluorocarbon and hydrochlorofluorocarbon alkene and alkyne intermediates which serve as useful feedstock for fluorination and reduction to cis-1,1,1,4,4,4-hexafluoro-2-butene. Also presented is a continuous process for the production of cis-1,1,1,4,4,4-hexafluoro-2-butene from the alkene and alkyne intermediates.

One embodiment of the invention is directed to a process for the manufacture of cis-1,1,1,4,4,4-hexafluoro-2-butene comprising the steps of:

(a) contacting a haloalkane compound with hexafluoropropene at a temperature effective to facilitate an addition reaction to form an intermediate hydrofluorochlorobutane;

(b) contacting HF with the hydrofluorochlorobutane formed in step (a) under conditions effective to facilitate the fluorination of the butane compound and produce an effluent stream comprising a compound selected from the group consisting of a hydrofluorobutane, a hydrofluorobutene, or a mixture thereof;

(c) contacting the reaction product of step (b) with a metal catalyst and hydrogen under conditions effective to dehydrohalogenate the reaction product of step (b) to form a compound selected from the group consisting of a hydrofluorobutene, a fluorobutyne, or a mixture thereof;

(d) recycling the reaction products of step (c) through the hydrogenation process to essentially complete the conversion of the hydrofluorobutene into the hexafluorobutyne; and (e) selectively reducing the hexafluorobutyne to produce cis-1,1,1,4,4,4-hexafluoro-2-butene.

Another embodiment of the present invention is a continuous process for the manufacture of fluorinated butenes, and in particular cis-1,1,1,4,4,4-hexafluoro-2-butene (HFO-1336), from readily available raw material, hexafluoropropene and haloalkanes of the general formula:

$$CX_nY_mZ_o$$

wherein X, Y and Z are each independently selected from the group consisting of H, Cl and F and wherein the sum total of n+m+o=4.

Typical compounds conforming to the above general formula are $CH_3Cl$, $CH_2Cl_2$, $CHCl_3$, $CCl_4$, $CH_3F$, $CH_2F_2$, $CHF_2Cl$, and the like. Addition of such compounds to hexafluoropropene thermally is described in J. Fluorine Chemistry 1982, 21, 253-259. For example, $CH_2Cl_2$ addition to $CF_3CF=CF_2$ at 280° C. is reported to give 85% yield of $CHCl_2CF_2CHFCF_3$.

The hexafluoro-2-butene is produced via either the chlorination, fluorination or dehydrohalogenation and combinations of these reaction steps from the intermediates generated from the addition reaction of hexafluoropropene and haloalkanes including $CH_2ClCF_2CHFCF_3$, $CHCl_2CF_2CHFCF_3$, $CCl_3CF_2CHFCF_3$, $CH_2FCF_2CHFCF_3$, $CHF_2CF_2CHFCF_3$, and $CF_2ClCF_2CHFCF_3$. Isolation of the butene is accomplished via distillation and any unreacted starting materials are recycled through the reactor.

DETAILED DESCRIPTION OF THE INVENTION

Starting with chloroform and hexafluoropropene, 1,1,1,4,4,4-hexafluoro-2-butene can be prepared through the following steps $$CHCl_3 + CF_3CF=CF_2 \rightarrow CCl_3CF_2CHFCF_3 \quad (1)$$

$$CCl_3CF_2CHFCF_3 + HF \rightarrow CF_3CF_2CHFCF_3 + HCl \quad (2)$$

$$CF_3CF_2CHFCF_3 \rightarrow CF_3CF=CFCF_3 + CF_3C\equiv CCF_3 \quad (3)$$

$$CF_3CF=CFCF_3 + CF_3C\equiv CCF_3 + H_2 \rightarrow CF_3CH=CHCF_3 \quad (4)$$

Reaction steps (1) and (2) are preferably carried out in a continuous fashion. In reaction step (1), chloroform and hexafluoropropene are co-fed into a heated reactor tube at such a rate and temperature as to give the desired product with minimal side product formation. The reaction temperature can range from 250° C. to 350° C. and preferably from 275° C. to 290° C.

The reactor tube can be optionally packed with Helipack Monel or stainless steel packing as a convenient means to adjust the contact time of the reagents. Contact times tend to vary with the haloalkane reagents employed and typically vary from 10 seconds to 10 hours. The pressure is also adjusted to achieve the desired contact times. Generally, the reaction pressure is maintained between 1 and 400 psig, preferably 50-200 psig. The reactor effluent is fed to a separation column to ensure that separation of reactants from product(s) is complete.

In step (2), the $CCl_3CF_2CHFCF_3$ is reacted with HF in the presence of a fluorination catalyst under conditions effective to facilitate a fluorination reaction and to form a product stream comprising $CF_3CF_2CHFCF_3$. The effluent stream from the reactor may optionally contain additional components such as unreacted HF and CCl$_3$CF$_2$CHFCF$_3$ or partially fluorinated derivatives thereof. The fluorination process may be carried out in the vapor phase or in the liquid phase.

In the vapor phase fluorination, HF is fed continuously through the catalyst bed. After a short time with only HF in the feed stream, CCl$_3$CF$_2$CHFCF$_3$ is fed continuously through the catalyst bed at a ratio of about 1:6 to about 1:30, preferably from about 1:10 to about 1:20. The reaction is carried out at a temperature from about 100° C. to 500° C., preferably from about 200° C. to about 350° C.; and at a pressure of about 5 psig to 200 psig, preferably from about 20 psig to about 100 psig. Suitable vapor phase solid catalysts include, but are not limited to chromium, aluminum, cobalt, nickel, and iron oxide, hydroxides, halides, oxyhalides, inorganic salts thereof and their mixtures.

Chromium(III) oxides such as crystalline chromium oxide or amorphous chromium oxide are most preferred, Chromium oxide is a commercially available material which may be purchased in a variety of particle sizes. The catalyst may be supported on a substrate such as activated carbon. In addition to activated carbon, useful catalyst supports include alumina, fluorinated alumina, aluminum fluoride, alkaline earth metal oxides, fluorinated alkaline earth metal oxides, zinc oxide, zinc fluoride, tin oxide, and tin fluoride. Optionally, but preferably, these catalysts are subjected to fluorination treatment with HF prior to introduction of the organic. Optionally, the catalysts may be unsupported or free standing.

In liquid phase fluorinations, a liquid phase fluorination catalyst is charged to a reactor. Possible fluorination catalysts for liquid phase reactions include but are not limited to Lewis acids, transition metal halides and oxides, Group IVb metal halides, and Group Vb metal halides or combinations thereof. Suitable liquid phase fluorination catalysts include antimony halides, tin halides, tantalum halides, titanium halides, niobium halides, molybdenum halides, iron halides, fluorinated chromium halides or combinations thereof. Specific non-exclusive examples are SbF$_5$, SbCl$_3$, SbCl$_5$, SnCl$_4$, TaCl$_5$, TiCl$_4$, MoCl$_6$FeCl$_3$, a fluorinated species of SbCl$_5$, a fluorinated species of SbCl$_3$, a fluorinated species of SnCl$_4$, a fluorinated species of TaCl$_5$, a fluorinated species of TiCl$_4$, a fluorinated species of NbCl$_5$, a fluorinated species of MoCl$_6$, a fluorinated species of FeCl$_3$, or combinations thereof.

The activated catalyst is then heated to the desired reaction temperature of from about 30° C. to about 200° C., preferably from about 50° C. to 120° C.; and at a pressure between 15 psig to about 200 psig, preferably from 50 psig to about 175 psig. CCl$_3$CF$_2$CHFCF$_3$ is fed continuously through the catalyst at a ratio of about 1:6 to about 1:30 and preferably from about 1:10 to about 1:20. If necessary, the catalyst can be kept activated by the continuous or batch addition of Cl$_2$ or similar oxidizing agent. The fluorination reaction is preferably carried out to achieve conversion of about 70% or more, preferably 90% or more, and most preferably 95% or more.

The fluorination is carried out in a corrosion resistant vessel. Examples of corrosion resistant vessels include Hastelloy, Nickel, Incoloy, Inconel, Monel and fluoropolymer lined vessels. The vessel may have a fixed bed, or contain liquid catalyst. If desired, inert gases such as nitrogen or argon may be employed in the reactor during operation. Preferably, the reactor effluent is fed to a caustic scrubber or to a distillation column to remove by-product HCl and unreacted HF to produce an acid free organic product which may optionally undergo further purification.

In step (3), the organic produced above is fed into a vapor phase reactor which contains a dehydrohalogenation catalyst which produces CF$_3$CF=CFCF$_3$ and CF$_3$C≡CCF$_3$. The catalysts for this process may be metal halides, halogenated metal oxides, metals in the zero valence state, metal alloys, and supported metal species. Components of the metal halides or the metal oxides can consist of but are not limited to Cr$^{3+}$, Fe$^{3+}$, Mg$^{2+}$, Ca$^{2+}$, Ni$^{2+}$, Zn$^{2+}$, Pd$^{2+}$, Li$^+$, Na$^+$, Cs$^+$. Component halogens can include F$^-$, Cl$^-$, Br$^-$, and I$^-$. In the zero valent state useful metals include but are not limited to Pd, Pt, Rh, Fe, Co, Ni, Cu, Mo, Cr, Mn, and combinations thereof. The catalysts may be supported or unsupported.

The reaction temperatures for the dehydrohalogenation can range from 150° C. to about 600° C. preferably from about 200° C. to about 500° C., and most preferably from about 250° C. to about 400° C. The reaction pressure is preferably from about 1 psig to 150 psig. The reactor effluent is fed to a caustic scrubber or to a distillation column to remove the acid by-product which then yields an acid free organic product, CF$_3$CF=CFCF$_3$ and CF$_3$C≡CCF$_3$.

The CF$_3$CF=CFCF$_3$ and CF$_3$C≡CCF$_3$ product mixture may be further reacted with more hydrogen to produce exclusively hexafluoro-2-butyne, CF$_3$C≡CCF$_3$ which can readily be converted into the cis-1,1,1,4,4,4-hexafluoro-2-butene product. This second dehydrohalogenation reaction may be carried out under the same reaction conditions and with the same catalysts as described above for the first dehydrohalogenation reaction.

The hexafluorobutyne can be selectively reduced to the cis-hexafluoro-2-butene by utilizing the procedure detailed by Van Der Puy et al. entitled "Process for the Preparation of Fluorinated Cis-Alkene" filed as U.S. Provisional Application No. 61/085,077, the disclosure of which is hereby incorporated herein by reference.

It should be noted that CHCl$_3$ can also be added another way, and hexafluorobutene can be made as follows:

   (a)

   (b)

   (c)

   (d)

By extension of the chemistry and with selection of a different haloalkane compound, the following intermediates which serve as useful precursors to the preparation of 1,1,1,4,4,4-hexafluorobutyne can be prepared:

(a) CCl$_3$CF$_2$CHFCF$_3$ from the chlorination of CH$_2$ClCF$_2$CHFCF$_3$ obtained by the addition of CH$_3$Cl to hexafluoropropene;

(b) CCl$_3$CF$_2$CHFCF$_3$ from the chlorination of CHCl$_2$CF$_2$CHFCF$_3$ obtained by the addition of CH$_2$Cl$_2$ to hexafluoropropene;

(c) CCl$_2$FCF$_2$CHFCF$_3$ from the chlorination of CH$_2$FCF$_2$CHFCF$_3$ obtained by the addition of CH$_3$F to hexafluoropropene; and (d) CClF$_2$CF$_2$CHFCF$_3$ from the chlorination of CHF$_2$CF$_2$CHFCF$_3$ obtained by the addition of CH$_2$F$_2$ to hexafluoropropene.

The following examples are provided to further illustrate the invention and should not be taken as limitations of the invention.

Example 1

Preparation of CCl$_3$CF$_2$CHFCF$_3$

A 0.5 inch (12.7 mm) by 40 inch (101.6 cm) plug flow reactor that is packed with Helipack Monel support is heated to 290° C. A 50/50 (molar %) mixture of hexafluoropropene and chloroform is fed into the reactor at about 1.5 g/min. The reactor pressure is maintained at 100 psig. The effluent from the reactor is fed into a distillation column and the unreacted reagents removed by distillation and recycled. The product $CCl_3CF_2CHFCF_3$ is used in the next reaction.

Example 2

Preparation of $CF_3CF_2CHFCF_3$ by Liquid Phase Fluorination

The liquid phase fluorination of $CCl_3CF_2CHFCF_3$ is conducted in the presence of $SbCl_5$. About 600 g of $SbCl_5$ are added to a liquid phase reactor. The reactor is heated to from 80° C. to 90° C. and the HF feed is started. After about 0.1 lbs (4.54 kg) of HF are added, the $CCl_3CF_2CHFCF_3$ feed is started. The corresponding feeds for the HF and organic are about 0.05 lb/h (2.27 kg/hr) and 0.04 lb/h (1.8 kg/hr) respectively. The average pressure for the system during the reaction is about 100 psig (689.5 kPa).

Example 3

Dehydrohalogenation

A Hastelloy-C reactor is charged with 50 cc of a Ni—Cu—Cr catalyst and pretreated with hydrogen gas for two hours at 400° C. While maintaining a hydrogen atmosphere, the organic compound, $CF_3CF_2CHFCF_3$ is vaporized into the reactor such that the $H_2$ to organic molar ratio is at least 2:1. The olefin products are collected in a cold trap, and then recycled thru the reactor system in order to complete the conversion of the organic compound into the butyne product.

Example 4

Selective Preparation of cis-1,1,1,4,4,4-hexafluoro-2-butene

A 1-liter autoclave is charged with 2.0 g of catalyst (5% palladium on calcium carbonate poisoned with 3.5% lead) and 160 mL ethanol. The autoclave contents are then cooled to −78° C. Air was removed by pressurizing to 60 psi (434 kPa) with nitrogen followed by evacuating. The air removal sequence is repeated twice more. Hexafluoro-2-butyne (32 g) is then added and the contents warmed to 25° C. Hydrogen gas is added to a pressure 90 psig (651 kPa) and is maintained at this pressure for approximately 20 hours at a reaction temperature of from 25° C. to 28° C. The autoclave contents are again cooled with the aid of a −78° C. bath prior to venting the hydrogen gas. The material in the autoclave is distilled to give 31.6 g of 97% pure cis-hexafluoro-2-butene (97.5% yield).

Three such preparations are made and the combined materials redistilled to give the desired butene, by 30° C. to 32° C., in greater than 99.9% purity ($^1$H NMR: 6.56 ppm; $^{19}$F NMR: −60.17 ppm).

While the present invention has been particularly shown and described with reference to preferred embodiments, it will be readily appreciated by those of ordinary skill in the art that various changes and modifications may be made without departing from the scope of the invention. It is intended that the claims be interpreted to cover the disclosed embodiment, those alternatives which have been discussed above and all equivalents thereto.

What is claimed is:

1. A process for the manufacture of 1,1,1,4,4,4-hexafluoro-2-butene comprising the steps of:
   (a) contacting a haloalkane compound with hexafluoropropene at a temperature effective to facilitate an addition reaction to form an intermediate hydrofluorochlorobutane;
   (b) contacting HF with the intermediate hydrofluorochlorobutane formed in step (a) under conditions effective to facilitate the fluorination of the butane compound and produce an effluent stream comprising a compound selected from the group consisting of a hydrofluorobutane, a hydrofluorobutene, and mixtures thereof;
   (c) contacting the reaction product of step (b) with a metal catalyst and hydrogen under conditions effective to dehydrohalogenate the reaction product of step (b) to form a compound selected from the group consisting of a hydrofluorobutene, a fluorobutyne, and mixtures thereof;
   (d) recycling the reaction products of step (c) through the hydrogenation process to convert the hydrofluorobutene into hexafluorobutyne; and
   (e) selectively reducing the hexafluorobutyne to produce the cis-1,1,1,4,4,4-hexafluoro-2-butene.

2. The process of claim 1, wherein steps (a) and (b) are carried out in a continuous fashion.

3. The process of claim 1, wherein the haloalkane compound has the formula:

$$CX_nY_mZ_o$$

wherein X, Y and Z are each independently selected from the group consisting of H, Cl and F and wherein the sum total of n+m+o=4.

4. The process of claim 3, wherein the haloalkane compound is selected from the group consisting of $CH_3Cl$, $CH_2Cl_2$, $CHCl_3$, $CCl_4$, $CH_3F$, $CH_2F2$, and $CHF_2Cl$.

5. The process of claim 1, wherein the intermediate hydrofluorochlorobutane is selected from the group consisting of $CH_2ClCF_2CHFCF_3$, $CHCl_2CF_2CHFCF_3$, $CCl_3CF_2CHFCF_3$, $CH_2FCF_2CHFCF_3$, $CHF_2CF_2CHFCF_3$, and $CF_2ClCF_2CHFCF_3$.

6. A process for the manufacture of fluorinated butenes comprising the steps of:
   (a) an addition reaction between hexafluoropropene and a haloalkane compound having the formula:

$$CX_nY_mZ_o$$

wherein X, Y and Z are each independently selected from the group consisting of H, Cl and F and wherein the sum total of n+m+o=4 to produce an intermediate hydrofluorochlorobutane compound; and
   (b) subjecting the intermediate hydrofluorochlorobutane compound to a reaction selected from the group consisting of chlorination, fluorination, dehydrohalogenation and one or more combinations of these reactions, to form one or more fluorinated butene compound.

7. The process of claim 6, wherein the step (b) reaction comprises the chlorination of the intermediate hydrofluorochlorobutane compound.

8. The process of claim 6, wherein the step (b) reaction comprises the fluorination of the intermediate hydrofluorochlorobutane compound.

9. The process of claim 6, wherein the step (b) reaction comprises the dehydrohalogenation of the intermediate hydrofluorochlorobutane compound.

10. The process of claim 6, further comprising step (c), the isolation of the fluorinated butene compound.

11. The process of claim 10, wherein the isolation of the fluorinated butene compound is by distillation.

12. The process of claim 10, wherein any unreacted starting materials are recycled.

13. The process of claim 6, wherein the fluorinated butene compound is cis-1,1,1,4,4,4-hexafluorobutene (HFO-1336).

* * * * *